US011400186B2

(12) United States Patent
Barrett et al.

(10) Patent No.: US 11,400,186 B2
(45) Date of Patent: Aug. 2, 2022

(54) DRUG DELIVERY SYSTEM FOR THE DELIVERY OF ANTIVIRAL AGENTS

(71) Applicants: Stephanie Elizabeth Barrett, Quakertown, PA (US); Marian E. Gindy, North Wales, PA (US); Li Li, North Wales, PA (US); Ryan S. Teller, Doylestown, PA (US); Seth P. Forster, Fort Washington, PA (US); Merck Sharp & Dohme Corp., Rahway, NJ (US)

(72) Inventors: Stephanie Elizabeth Barrett, Quakertown, PA (US); Marian E. Gindy, North Wales, PA (US); Li Li, North Wales, PA (US); Ryan S. Teller, Doylestown, PA (US); Seth P. Forster, Fort Washington, PA (US)

(73) Assignee: Merck Sharp & Dohme LLC, Rahway, NJ (US)

( * ) Notice: Subject to any disclaimer, the term of this patent is extended or adjusted under 35 U.S.C. 154(b) by 0 days.

(21) Appl. No.: 16/300,121

(22) PCT Filed: May 8, 2017

(86) PCT No.: PCT/US2017/031493
§ 371 (c)(1),
(2) Date: Nov. 9, 2018

(87) PCT Pub. No.: WO2017/196697
PCT Pub. Date: Nov. 16, 2017

(65) Prior Publication Data
US 2019/0388590 A1 Dec. 26, 2019

Related U.S. Application Data

(60) Provisional application No. 62/335,319, filed on May 12, 2016.

(51) Int. Cl.
| A61L 27/54 | (2006.01) |
| A61K 9/00 | (2006.01) |
| A61K 31/7076 | (2006.01) |
| A61K 47/32 | (2006.01) |
| A61K 47/34 | (2017.01) |
| A61L 27/16 | (2006.01) |

(52) U.S. Cl.
CPC ............ *A61L 27/54* (2013.01); *A61K 9/0024* (2013.01); *A61K 31/7076* (2013.01); *A61K 47/32* (2013.01); *A61K 47/34* (2013.01); *A61L 27/16* (2013.01)

(58) Field of Classification Search
None
See application file for complete search history.

(56) References Cited

U.S. PATENT DOCUMENTS

| 5,633,000 | A | 5/1997 | Grossman et al. |
| 6,262,137 | B1 * | 7/2001 | Kozma ..................... C08F 8/00 521/134 |
| 8,722,037 | B2 * | 5/2014 | Veenstra ............ A61K 49/0409 424/94.1 |
| 8,835,615 | B2 * | 9/2014 | Chang ..................... A61P 31/18 536/22.1 |
| 2004/0175426 | A1 | 9/2004 | Ashton |
| 2010/0080830 | A1 | 4/2010 | Ashton et al. |
| 2011/0206745 | A1 | 8/2011 | Kuzma et al. |
| 2013/0195950 | A1 | 8/2013 | Patel et al. |
| 2015/0051167 | A1 | 2/2015 | Wang et al. |
| 2015/0297553 | A1 | 10/2015 | Brown |

FOREIGN PATENT DOCUMENTS

| GB | 2 168 257 | * | 6/1986 | ............... A61F 5/47 |
| RU | 2157246 C2 | | 10/2000 | |
| WO | WO 2004/103336 | * | 12/2004 | ............... A61K 9/00 |
| WO | WO 2014/123880 | * | 8/2014 | ........... A61K 31/731 |
| WO | 2015086489 A1 | | 6/2015 | |
| WO | 2016149561 A1 | | 9/2016 | |
| WO | 2017222903 A1 | | 12/2017 | |
| WO | 2018057408 A1 | | 3/2018 | |
| WO | 2018191093 A1 | | 10/2018 | |

OTHER PUBLICATIONS

Kleppner et al (J Pharmacy and Pharmacol 58:295-302, 2006) (Year: 2006).*
Gunawardana et al (Antimicrobial Agents and Chemotherapy 59:3913-3919, 2015) (Year: 2015).*
Reyes (Innovative Uses of EVA Polymers for Advancing Healthcare, 2014) (Year: 2014).*
Zhang et al (Drug Development and Industrial Pharmacy 40(8):1101-1111, 2014) (Year: 2014).*
Baert, L. et al., Development of a long-acting injectable formulation with nanoparticles of rilpivirine (TMC278) for HIV treatment, European Journal of Pharmaceutics and Biopharmaceutics, 2009, 502-208, 72 (3).
Gunawardana, M. et al., Pharmacokinetics of Long-Acting Tenofovir Alafenamide (GS-7340) Subdermal Impant for HIV Prophylaxis, Antimicrob. Agents Chemother., 2015, 3913-3919, 59 (7).
International Search Report and Written Opinion for PCT/2017/031493, dated Aug. 15, 2017, 8 pages.
Karmon, S.L et al., Next-Generation Integrase Inhibitors Where to After Raltegravir, Drugs, 2013, 213-228, 73 (3).
Rajoli, R.K.R. et al., Physiologically Based Pharmacokinetic Modelling to Inform Development of Intramuscular Long-Acting Nanoformulations for HIV, Clinical Pharmacokinetics, 2015, 639-650, 54 (6).
Ramirez Garcia, P. et al., Factors affecting adherence to antiretroviral therapy in people living with HIV/AIDS, The Journal of Association of Nurses in AIDS Care : JANAC, 2003, 37-45, 14 (4).

(Continued)

*Primary Examiner* — Craig D Ricci
(74) *Attorney, Agent, or Firm* — Daniel Woods; John C. Todaro

(57) ABSTRACT

This invention relates to novel implant drug delivery systems for long-acting delivery of antiviral drugs. These compositions are useful for the treatment or prevention of human immunodeficiency virus (HIV) infection.

9 Claims, 1 Drawing Sheet

(56) References Cited

OTHER PUBLICATIONS

Spreen, W.R. et al., Long-acting injectable antiretrovirals for HIV treatment and prevention, Current Opinion in HIV and AIDS, 2013, 565-571, 8 (6).
Van't Klooster G. et al., Pharmacokinetics and Disposition of Rilpivirine (TMC278) Nanosuspension as a Long-Acting Injectable Antiretroviral Formulation, Antimicrobial Agents and Chemotherapy, 2010, 2042-2050, 54 (5).
Whetten, K et al., Trauma, mental health, distrust, and stigma among HIV-Positive persons: Implications for effective care., Psychosomatic Medicine, 2008, 70.
Williams, J. et al., Long-acting parenteral nanoforulated antiretroviral therapy: interest and attitudes of HIV-infected patients, Nanomedicine, 2013, 1807-1813, 8 (11).
Supplementary European Search Report and Written Opinion for 17796613.2, dated Nov. 20, 2019, 9 pages.
Brazel, Christopher et al., Mechanisms of solute and drug transport in relaxing, swellable, hydrophilic glassy polymers, Polymer, 1999, 3383-3398, 40.
Grigoreva, M.V., Polymer systems with the controlled release of biologically active compounds, Biotechnologia Acta, 2011, 9-23 (English translation pp. 1-31), 4(2).
Grigoreva, M.V., Polymer systems with the controlled release of biologically active compounds, Biotechnologia Acta, 2011, 9-23, 4(2).
Sysuev, B.B et al., Current research and development of innovative dosage forms and their modifications, Bulletin of Volgogradskyi State Medical University, 2014, 7-12 (English translation pp. 1-13), 4(52).
Sysuev, B.B et al., Current research and development of innovative dosage forms and their modifications, Bulletin of Volgogradskyi State Medical University, 2014, 7-12, 4(52).
Barrett, Stephanie et al., Extended-Duration MK-8591-Eluting Implant as a Candidate for HIV Treatment and Prevention, Antimicrobial Agents and Chemotherapy, 2018, 1-13, vol. 62(10), e01058-18.
Zhang, Wei et al., Preformulation studies of EFdA, a novel nucleoside reverse transcriptase inhibitor for HIV prevention, Drug Development and Industrial Pharmacy, 2014, 1101-1111, 40:8.

* cited by examiner

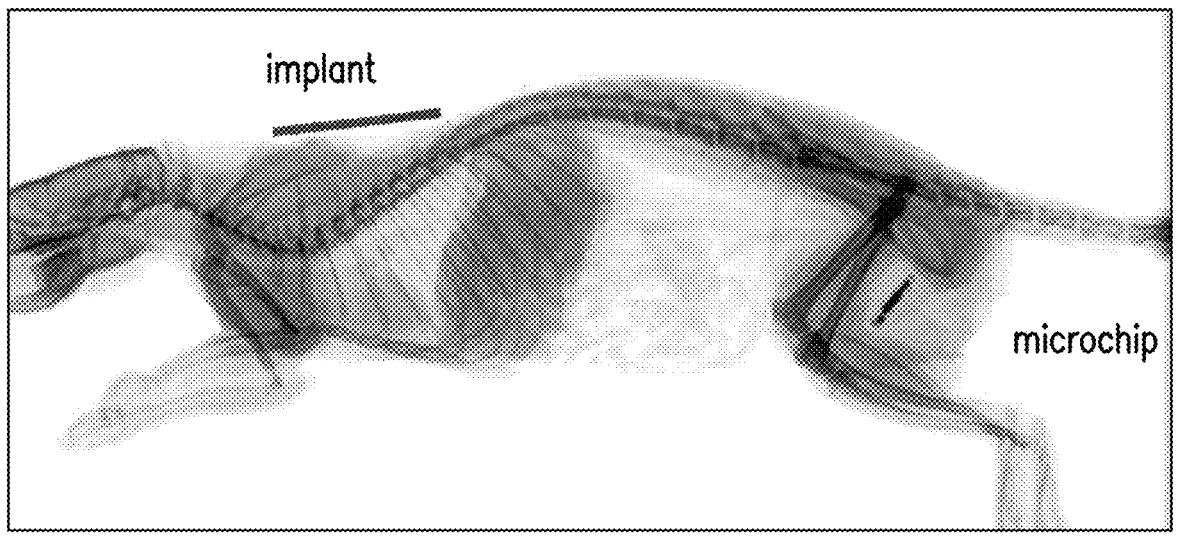

DRUG DELIVERY SYSTEM FOR THE DELIVERY OF ANTIVIRAL AGENTS

CROSS REFERENCE TO RELATED APPLICATIONS

This application is a U.S. National Phase application under 35 U.S.C. § 371 of PCT Application No. PCT/US2017/031493 filed May 8, 2017, which claims priority from U.S. Ser. No. 62/335,319 filed May 12, 2016.

BACKGROUND OF THE INVENTION

The development of highly active antiretroviral therapy (HAART) in the mid 1990's transformed the clinical care of human immunodeficiency virus (HIV) type I infection. HAART regimens have proven to be highly effective treatments, significantly decreasing HIV viral load in HIV-infected patients, thereby slowing the evolution of the illness and reducing HIV-related morbidity and mortality. Yet, the treatment success of HAART is directly related to adherence to the regimen by the patient. Unless appropriate levels of the antiretroviral drug combinations are maintained in the blood, viral mutations will develop, leading to therapy resistance and cross-resistances to molecules of the same therapeutic class, thus placing the long-term efficacy of treatments at risk. Various clinical studies have shown a decline in treatment effectiveness with relatively small lapses in adherence. A study by Musiime found that 81% of patients with more than 95% adherence demonstrated viral suppression, while only 50% of patients who were 80-90% adherent were successful. See, Musiime, S., et al., Adherence to Highly Active Antiretroviral Treatment in HIV-Infected Rwandan Women. *PLOS one* 2011, 6, (11), 1-6. Remarkably, only 6% of patients that were less than 70% adherent showed improvements in viral markers. Thus, low adherence is a leading cause of therapeutic failure in treatment of HIV-1 infection.

Nonetheless, adherence rates to the HAART regimens continue to be far from optimal. Various characteristics of HAART make adherence particularly difficult. Therapeutic regimens are complex, requiring multiple drugs to be taken daily, often at different times of the day, and many with strict requirements on food intake. Many HAART medications also have unpleasant side effects, including nausea, diarrhea, headache, and peripheral neuropathy. Social and psychological factors can also negatively impact adherence. Patients report that forgetfulness, lifestyle factors, including fear of being identified as HIV-positive, and therapy fatigue over life-long duration of treatment all contribute to adherence lapses.

New HIV treatment interventions aim to improve adherence by reducing the complexity of treatments, the frequency of the dosages, and/or the side effects of the medications. Long-acting injectable (LAI) drug formulations that permit less frequent dosing, on the order of a month or longer, are an increasingly attractive option to address adherence challenges. However, the majority of approved and investigational antiretroviral agents are not well suited for reformulation as long-acting injectable products. In large part, this is due to suboptimal physicochemical properties limiting their formulation as conventional drug suspensions, as well as insufficient antiviral potency resulting in high monthly dosing requirements. Even for cabotegravir or rilpivirine, two drugs being studied as long-acting injectible formulations, large injection volumes and multiple injections are required to achieve pharmacokinetic profiles supportive of monthly dosing. See, e.g., Spreen, W. R., et al., Long-acting injectable antiretrovirals for HIV treatment and prevention. *Current Opinion in Hiv and Aids* 2013, 8, (6), 565-571; Rajoli, R. K. R., et al., Physiologically Based Pharmacokinetic Modelling to Inform Development of Intramuscular Long-Acting Nanoformulations for HIV. *Clinical Pharmacokinetics* 2015, 54, (6), 639-650; Baert, L., et al., Development of a long-acting injectable formulation with nanoparticles of rilpivirine (TMC278) for HIV treatment. *European Journal of Pharmaceutics and Biopharmaceutics* 2009, 72, (3), 502-508; Van't Klooster, G., et al., Pharmacokinetics and Disposition of Rilpivirine (TMC278) Nanosuspension as a Long-Acting Injectable Antiretroviral Formulation. *Antimicrobial Agents and Chemotherapy* 2010, 54, (5), 2042-2050. Thus, novel formulation approaches capable of delivering extended-duration pharmacokinetic characteristics for molecules of diverse physicochemical properties at practical injection volumes and with a limited number of injections are highly desirable.

SUMMARY OF THE INVENTION

This invention relates to novel implant drug delivery systems for long-acting delivery of antiviral drugs. These compositions are useful for the treatment or prevention of human immunodeficiency virus (HIV) infection.

BRIEF DESCRIPTION OF THE DRAWINGS

FIG. 1. X-ray image of a barium sulfate containing implant in a rat (image taken after a 6 month duration in vivo).

DETAILED DESCRIPTION OF THE INVENTION

This invention relates to novel implant drug delivery systems for long-acting delivery of antiviral drugs. The novel implant drug delivery systems comprise a polymer and an antiviral agent. These implant drug delivery systems are useful for the treatment or prevention of human immunodeficiency virus (HIV) infection. The invention further relates to methods of treating and preventing HIV infection with the novel implant drug delivery systems described herein.

The novel implant delivery systems of the invention comprise a biocompatible nonerodible polymer to generate monolithic matrices with dispersed or dissolved drug. The chemical properties of the polymer matrices are tuned to achieve a range of drug release characteristics, offering the opportunity to extend duration of dosing. In an embodiment of the invention, the novel implant delivery systems are compatible with molecules having a broad spectrum of physicochemical properties, including those of high aqueous solubility or amorphous phases which are unsuitable to formulation as solid drug suspensions.

Specifically, this invention relates to novel implant drug delivery systems comprising a biocompatible nonerodible polymer and 4'-ethynyl-2-fluoro-2'-deoxyadenosine wherein said implant drug delivery system is implanted subdermally and 4'-ethynyl-2-fluoro-2'-deoxyadenosine is continually released in vivo at a rate resulting in a plasma concentration between 0.01 ng/mL and 3000.0 ng/mL. These implant delivery systems are desired and useful for prophylaxis and/or treatment of HIV infection from both compliance and convenience standpoints.

As used herein, the term "biocompatible nonerodible polymer" refers to polymeric materials that are sufficiently resistant to degradation (both chemical and physical) in the presence of biological systems. Biocompatible nonerodible polymers are sufficiently resistant to chemical and/or physical destruction by the environment of use such that the polymer remains essentially intact throughout the release period. The polymer is generally hydrophobic so that it retains its integrity for a suitable period of time when placed in an aqueous environment, such as the body of a mammal, and stable enough to be stored for an extended period before use. Nonerodible polymers remain intact in vivo for extended periods of time, typically months or years. Drug molecules encapsulated in the polymer are released over time via diffusion through channels and pores in a sustained manner. The release rate can be altered by modifying the percent drug loading, porosity of the polymer, structure of the implantable device, or hydrophobicity of the polymer, or by adding a coating to the exterior of the implantable device.

Accordingly, any polymer that cannot be absorbed by the body can be used to manufacture the implant drug delivery systems of the instant invention that comprise a biocompatible nonerodible polymer. Biocompatible nonerodible polymers of the instant invention include, but are not limited to, ethylene vinyl acetate copolymer (EVA), poly(urethane), silicone, hydrogels such as crosslinked poly(vinyl alcohol) and poly(hydroxy ethylmethacrylate), acyl substituted cellulose acetates and alkyl derivatives thereof, partially and completely hydrolyzed alkylene-vinyl acetate copolymers, unplasticized polyvinyl chloride, crosslinked homo- and copolymers of polyvinyl acetate, crosslinked polyesters of acrylic acid and/or methacrylic acid, polyvinyl alkyl ethers, polyvinyl fluoride, polycarbonate, polyamide, polysulphones, styrene acrylonitrile copolymers, crosslinked poly(ethylene oxide), poly(alkylenes), poly(vinyl imidazole), poly(esters), poly(ethylene terephthalate), polyphosphazenes, and chlorosulphonated polylefins, and combinations thereof. In a class of the invention, the biocompatible nonerodible polymer is ethylene vinyl acetate copolymer (EVA).

In a class of the invention, the biocompatible nonerodible polymer is selected from the group consisting of ethylene vinyl acetate copolymer (9% vinyl acetate), ethylene vinyl acetate copolymer (15% vinyl acetate), ethylene vinyl acetate copolymer (28% vinyl acetate), and ethylene vinyl acetate copolymer (33% vinyl acetate). In a subclass of the invention, the biocompatible nonerodible polymer is ethylene vinyl acetate copolymer (9% vinyl acetate). In a subclass of the invention, the biocompatible nonerodible polymer is ethylene vinyl acetate copolymer (15% vinyl acetate). In a class of the invention, the biocompatible nonerodible polymer is poly(urethane).

As used herein, the term "diffusional barrier" refers to a coating that is permeable to the drug and is placed over at least a portion of the device to further regulate the rate of release. For example, a coating of biocompatible nonerodible polymeric material, e.g., EVA, or a coating of a biocompatible nonerodible polymeric material with a lower drug loading than the remainder of the implant delivery system, may be used. The diffusional barrier may be formed, for example, by coextrusion with the device.

Suitable diffusional barriers of the instant invention include, but are not limited to, ethylene vinyl acetate copolymer (EVA), poly(urethane), silicone, hydrogels such as crosslinked poly(vinyl alcohol) and poly(hydroxy ethylmethacrylate), acyl substituted cellulose acetates and alkyl derivatives thereof, partially and completely hydrolyzed alkylene-vinyl acetate copolymers, unplasticized polyvinyl chloride, crosslinked homo- and copolymers of polyvinyl acetate, crosslinked polyesters of acrylic acid and/or methacrylic acid, polyvinyl alkyl ethers, polyvinyl fluoride, polycarbonate, polyamide, polysulphones, styrene acrylonitrile copolymers, crosslinked poly(ethylene oxide), poly(alkylenes), poly(vinyl imidazole), poly(esters), poly(ethylene terephthalate), polyphosphazenes, and chlorosulphonated polylefins, and combinations thereof. In a class of the invention, the diffusional barrier is poly(urethane). In a class of the invention, the diffusional barrier is ethylene vinyl acetate copolymer (EVA). In another class of the invention, the diffusional barrier is poly(urethane).

In an embodiment of the invention, the diffusion barrier contains an antiviral drug. In a class of the embodiment, the diffusion barrier comprises 4'-ethynyl-2-fluoro-2'-deoxyadenosine.

As used herein, the term "dispersed or dissolved in the biocompatible nonerodible polymer" refers to the drug and polymer being mixed and then hot-melt extruded.

As used herein, the term "continually released" refers to the drug being released from the biocompatible nonerodible polymer at continuous rates for extended periods of time. The implant drug delivery systems of the instant invention generally exhibit linear release kinetics for the drug in vivo, sometimes after an initial burst.

Optionally, the novel implant delivery systems of the instant invention can further comprise a radiopaque component. The radiopaque component will cause the implant to be X-ray visible. The radiopaque component can be any such element known in the art, such as barium sulphate, titanium dioxide, bismuth oxide, tantalum, tungsten or platinum. In a specific embodiment, the radiopaque component is barium sulphate.

In one embodiment, the radiopaque material is about 1% to 30% by weight. In another embodiment, the radiopaque material is about 1% to 20% by weight. In another embodiment, the radiopaque material is about 4% to 25% by weight. In further embodiment, the radiopaque material is about 6% to 20% by weight. In another embodiment, the radiopaque material is about 4% to 15% by weight. In another embodiment, the radiopaque material is about 8% to 15% by weight.

The radiopaque material does not affect the release of 4'-ethynyl-2-fluoro-2'-deoxyadenosine from the implant.

The novel implant delivery systems of the invention comprise antiviral agents. Suitable antiviral agents include anti-HIV agents. In an embodiment of the invention, the antiviral agent is administered as a monotherapy. In another embodiment of the invention, two or more antiviral agents are administered in combination.

An "anti-HIV agent" is any agent which is directly or indirectly effective in the inhibition of HIV reverse transcriptase or another enzyme required for HIV replication or infection, or the prophylaxis of HIV infection, and/or the treatment, prophylaxis or delay in the onset or progression of AIDS. It is understood that an anti-HIV agent is effective in treating, preventing, or delaying the onset or progression of HIV infection or AIDS and/or diseases or conditions arising therefrom or associated therewith. Suitable anti-viral agents for use in implant drug delivery systems described herein include, for example, those listed in Table A as follows:

| Antiviral Agents for Preventing HIV infection or AIDS | |
|---|---|
| Name | Type |
| abacavir, ABC, Ziagen ® | nRTI |
| abacavir + lamivudine, Epzicom ® | nRTI |
| abacavir + lamivudine + zidovudine, Trizivir ® | nRTI |
| amprenavir, Agenerase ® | PI |
| atazanavir, Reyataz ® | PI |
| AZT, zidovudine, azidothymidine, Retrovir ® | nRTI |
| Capravirine | nnRTI |
| darunavir, Prezista ® | PI |
| ddC, zalcitabine, dideoxycytidine, Hivid ® | nRTI |
| ddI, didanosine, dideoxyinosine, Videx ® | nRTI |
| ddI (enteric coated), Videx EC ® | nRTI |
| delavirdine, DLV, Rescriptor ® | nnRTI |
| doravirine | nnRTI |
| efavirenz, EFV, Sustiva ®, Stocrin ® | nnRTI |
| efavirenz + emtricitabine + tenofovir DF, Atripla ® | nnRTI + nRTI |
| EFdA (4'-ethynyl-2-fluoro-2'-deoxyadenosine) | nRTI |
| emtricitabine, FTC, Emtriva ® | nRTI |
| emtricitabine + tenofovir DF, Truvada ® | nRTI |
| emvirine, Coactinon ® | nnRTI |
| enfuvirtide, Fuzeon ® | FI |
| enteric coated didanosine, Videx EC ® | nRTI |
| etravirine, TMC-125 | nnRTI |
| fosamprenavir calcium, Lexiva ® | PI |
| indinavir, Crixivan ® | PI |
| lamivudine, 3TC, Epivir ® | nRTI |
| lamivudine + zidovudine, Combivir ® | nRTI |
| Lopinavir | PI |
| lopinavir + ritonavir, Kaletra ® | PI |
| maraviroc, Selzentry ® | EI |
| nelfinavir, Viracept ® | PI |
| nevirapine, NVP, Viramune ® | nnRTI |
| PPL-100 (also known as PL-462) (Ambrilia) | PI |
| raltegravir, Isentress ™ | InI |
| (S)-2-(3-chloro-4-fluorobenzyl)-8-ethyl-10-hydroxy-N,6-dimethyl- | InI |
| ritonavir, Norvir ® | PI |
| saquinavir, Invirase ®, Fortovase ® | PI |
| stavudine, d4T, didehydrodeoxythymidine, Zerit ® | nRTI |
| tenofovir DF (DF = disoproxil fumarate), TDF, Viread ® | nRTI |
| Tenofovir, hexadecyloxypropyl (CMX-157) | nRTI |
| tipranavir, Aptivus ® | PI |
| Vicriviroc | EI |

EI = entry inhibitor; FI = fusion inhibitor; InI = integrase inhibitor; PI = protease inhibitor; nRTI = nucleoside reverse transcriptase inhibitor; nnRTI = non-nucleoside reverse transcriptase inhibitor.

Some of the drugs listed in the table can be used in a salt form; e.g., abacavir sulfate, delavirdine mesylate, indinavir sulfate, atazanavir sulfate, nelfinavir mesylate, saquinavir mesylate.

In certain embodiments the antiviral agents in the implant drug delivery systems described herein are employed in their conventional dosage ranges and regimens as reported in the art, including, for example, the dosages described in editions of the *Physicians' Desk Reference*, such as the 63rd edition (2009) and earlier editions. In other embodiments, the antiviral agents in the implant drug delivery systems described herein are employed in lower than their conventional dosage ranges. In other embodiments, the antiviral agents in the implant drug delivery systems described herein are employed in higher than their conventional dosage ranges.

In an embodiment of the invention, the antiviral agent can be an entry inhibitor; fusion inhibitor; integrase inhibitor; protease inhibitor; nucleoside reverse transcriptase inhibitor; or non-nucleoside reverse transcriptase inhibitor. In a class of the invention, the antiviral agent is a nucleoside reverse transcriptase inhibitor.

In an embodiment of the invention, the antiviral agent is a nucleoside reverse transciptase inhibitor (NRTI). In a class of the invention, the NRTI is 4'-ethynyl-2-fluoro-2'-deoxyadenosine.

4'-ethynyl-2-fluoro-2'-deoxyadenosine is also known as EFdA, and has the following chemical structure:

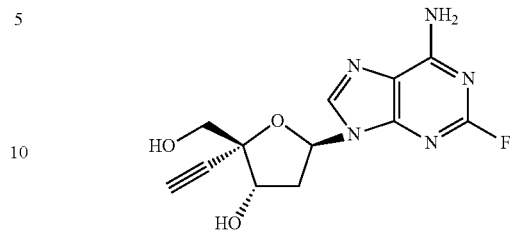

Production of and the ability of 4'-ethynyl-2-fluoro-2'-deoxyadenosine to inhibit HIV reverse transcriptase are described in PCT Internatinonal Application WO2005090349, published on Sep. 29, 2005, and US Patent Application Publication No. 2005/0215512, published on Sep. 29, 2005, both to Yamasa Corporation which are hereby incorporated by reference in its entirety.

In an embodiment of the implant drug delivery system described herein, the antiviral agent is present in the biocompatible nonerodible polymer at about 0.10%-80% by weight of drug loading. In other embodiments, the antiviral agent is present in the biocompatible nonerodible polymer at about 20%-60% by weight, at about 40%-60% by weight, at about 40%-50% by weight or at about 40%-45% by weight of drug loading. In a class of the embodiment of the implant drug delivery system described herein, 4'-ethynyl-2-fluoro-2'-deoxyadenosine is present in the biocompatible nonerodible polymer at about 0.10%-80% by weight of drug loading. In a subclass of the embodiment of the implant drug delivery system described herein, 4'-ethynyl-2-fluoro-2'-deoxyadenosine is present in the biocompatible nonerodible polymer at about 20%-60% by weight of drug loading. In a further subclass of the embodiment of the implant drug delivery system described herein, 4'-ethynyl-2-fluoro-2'-deoxyadenosine is present in the biocompatible nonerodible polymer at about 30%-65% by weight of drug loading. In a further subclass of the embodiment of the implant drug delivery system described herein, 4'-ethynyl-2-fluoro-2'-deoxyadenosine is present in the biocompatible nonerodible polymer at about 40%-60% by weight of drug loading. In a further subclass of the embodiment of the implant drug delivery system described herein, 4'-ethynyl-2-fluoro-2'-deoxyadenosine is present in the biocompatible nonerodible polymer at about 40%-50% by weight of drug loading. In a further subclass of the embodiment of the implant drug delivery system described herein, 4'-ethynyl-2-fluoro-2'-deoxyadenosine is present in the biocompatible nonerodible polymer at about 40%-45% by weight of drug loading. In an example of the embodiment of the implant drug delivery system described herein, 4'-ethynyl-2-fluoro-2'-deoxyadenosine is present in the biocompatible nonerodible polymer at 40% by weight of drug loading. In another example of the embodiment of the implant drug delivery system described herein, 4'-ethynyl-2-fluoro-2'-deoxyadenosine is present in the biocompatible nonerodible polymer at 45% by weight of drug loading. In another example of the embodiment of the implant drug delivery system described herein, 4'-ethynyl-2-fluoro-2'-deoxyadenosine is present in the biocompatible nonerodible polymer at 50% by weight of drug loading. In another example of the embodiment of the implant drug delivery system described herein, 4'-ethynyl-2-fluoro-2'-deoxyadenosine is present in the biocompatible nonerodible polymer at 60% by weight of drug loading. In another example of the embodiment of the implant drug delivery system described herein, 4'-ethynyl-2-fluoro-2'-deoxyadenosine is present in the biocompatible nonerodible polymer at 80% by weight of drug loading.

The implant drug delivery systems of the instant invention may be produced using an extrusion process, wherein ground biocompatible, nonerodible polymer is blended with the antiviral agent, melted and extruded into rod-shaped structures. Rods are cut into individual implantable devices of the desired length, packaged and sterilized prior to use. Other methods for encapsulating therapeutic compounds in implantable polymeric, nonerodible matrices are known to those of skill in the art. Such methods include solvent casting (see U.S. Pat. Nos. 4,883,666, 5,114,719 and 5,601835). One of skill in the art would be able to readily determine an appropriate method of preparing such an implant drug delivery system, depending on the shape, size, drug loading, and release kinetics desired for a particular type of patient or clinical application.

The size and shape of the implant drug delivery systems may be modified to achieve a desired overall dosage. The implant drug delivery systems of the instant invention are often about 0.5 cm to about 10 cm in length. In an embodiment of the invention, the implant drug delivery systems are about 1.5 cm to about 5 cm in length. In a class of the embodiment, the implant drug delivery systems are about 2 cm to about 5 cm in length. In a subclass of the embodiment, the implant drug delivery systems are about 2 cm to about 4 cm in length. The implant drug delivery systems of the instant invention are often about 0.5 mm to about 7 mm in diameter. In an embodiment of the invention, the implant drug delivery systems are about 1.5 mm to about 5 mm in diameter. In a class of the embodiment, the implant drug delivery systems are about 2 mm to about 5 mm in diameter. In a subclass of the embodiment, the implant drug delivery systems are about 2 mm to about 4 mm in diameter.

The implant drug delivery systems described herein are capable of releasing 4'-ethynyl-2-fluoro-2'-deoxyadenosine over a period of 21 days, 28 days, 31 days, 4 weeks, 6 weeks, 8 weeks, 12 weeks, one month, two months, three months, four months, five months, six months, seven months, eight months, nine months, ten months, eleven months, twelve months, eighteen months, twenty-four months or thirty-six months at an average rate of between 0.02-8.0 ng per day. In an embodiment of the invention, the 4'-ethynyl-2-fluoro-2'-deoxyadenosine is released at therapeutic concentrations for a duration from between three months and thirty-six months. In a class of the embodiment, the 4'-ethynyl-2-fluoro-2'-deoxyadenosine is released at therapeutic concentrations for a duration from between six months and twelve months. In an embodiment of the invention, the 4'-ethynyl-2-fluoro-2'-deoxyadenosine is released at prophylactic concentrations for a duration from between three months and thirty-six months. In a class of the embodiment, the 4'-ethynyl-2-fluoro-2'-deoxyadenosine is released at prophylactic concentrations for a duration from between six months and twelve months.

One or more implants can be used to achieve the desired therapeutic dose. In an embodiment of the invention, one or more implants can be used to achieve the therapeutic dose for durations of up to 1 year. In another embodiment of the invention, one or more implants can be used to achieve the therapeutic dose for durations of up to 2 years.

The implant drug delivery systems described herein are capable of releasing 4'-ethynyl-2-fluoro-2'-deoxyadenosine resulting in a plasma concentration of between 0.02-300 ng/mL per day. In an embodiment of the invention, the implant drug delivery systems described herein are capable of releasing 4'-ethynyl-2-fluoro-2'-deoxyadenosine resulting in a plasma concentration of between 0.02-30.0 ng/mL per day. In a class of the embodiment, the implant drug delivery systems described herein are capable of releasing 4'-ethynyl-2-fluoro-2'-deoxyadenosine resulting in a plasma concentration of between 0.02-15.0 ng/mL per day. In a further class of the embodiment, the implant drug delivery systems described herein are capable of releasing 4'-ethynyl-2-fluoro-2'-deoxyadenosine resulting in a plasma concentration of between 0.02-8.0 ng/mL per day. In a subclass of the embodiment, the implant drug delivery systems described herein are capable of releasing 4'-ethynyl-2-fluoro-2'-deoxyadenosine resulting in a plasma concentration of between 0.1-1.0 ng/mL per day.

The following examples are given for the purpose of illustrating the present invention and shall not be construed as being limitations on the scope of the invention.

EXAMPLE 1

Preparation and In Vitro Release of Implant Drug Delivery Systems Containing 30-50 Wt % 4'-Ethynyl-2-Fluoro-2'-Deoxyadenosine Implants were prepared using an extrusion process. The micronized polymer, and 4'-ethynyl-2-fluoro-2'-deoxyadenosine were blended at various ratios: 30, 35, 40, 45 and 50 wt % drug in EVA. The preblend was melt extruded with a twin screw extruder at temperatures ranging from 100-140° C., screw speed at 30 rpm, and then pelletized. The pellets were then extruded with a single screw extruder with temperatures ranging from 110-140° C., and screw speed at 20-25 rpm to form a 2±0.05 mm diameter filament, and then cut to a length of 40±2 mm.

The in vitro release rate of 4'-ethynyl-2-fluoro-2'-deoxyadenosine was determined by incubating the implants segments, approximately 1 cm in length, in a glass vial containing phosphate buffered saline (PBS) at 37° C., and 50 rpm shaking in an Innova 42 incubator. The volume of PBS was sufficient to maintain sink conditions. Sink conditions are defined as the drug concentration maintained at or below ⅓ of the maximum solubility (drug concentration ≤0.45 mg/mL in PBS at 37° C.). Samples were removed (0.5 mL) at selected time points, and centrifuged at 20,800×g for 8 min. The supernatant was removed (0.4 mL), diluted 4-fold, and vortexed. Samples were assayed by HPLC (Agilent 1100 series). Analysis of a 6 µL volume was performed at 240 nm with a Supelco Ascentis® Express C18 column (100×4.6 mm, 2.7 µm). The mobile phase was 0.1% $H_3PO_4$ and 50:50 ACN:MeOH (83:17 v/v) at a flow rate of 1.5 mL/min (40° C.).

To determine degradation of 4'-ethynyl-2-fluoro-2'-deoxyadenosine by HPLC, a 6 µL volume was injected onto an Agilent Zorbax SB-Aq column (150×4.6 mm, 3.5 µm). The mobile phase was 0.1% $H_3PO_4$ and 50:50 ACN:MeOH with a flow rate of 1.0 mL/min (40° C.). The mobile phase gradient is shown in the table below.

TABLE 1

| 4'-ethynyl-2-fluoro-2'-deoxyadenosine chemical stability HPLC method details | |
|---|---|
| Time (min) | 0.1% $H_3PO_4$ |
| 0.0 | 98 |
| 10.0 | 95 |
| 12.0 | 90 |
| 14.0 | 10 |
| 14.1 | 98 |
| 20.0 | 98 |

All samples were calibrated to 0.5 mg/mL standard solutions of 4'-ethynyl-2-fluoro-2'-deoxyadenosine in 50:50 MeOH:H$_2$O.

TABLE 2

4'-ethynyl-2-fluoro-2'-deoxyadenosine in vitro release from 30 wt %, 35 wt %, 40 wt %, 45 wt % and 50 wt % 4'-ethynyl-2-fluoro-2'-deoxyadenosine in EVA implants at sink conditions; reported as a % release from total [avg = average and std dev = standard deviation]

| Time (days) | 30 wt % EFdA + 70 wt % EVA | | 35 wt % EFdA + 65 wt % EVA | | 40 wt % EFdA + 60 wt % EVA | | 45 wt % EFdA + 55 wt % EVA | | 50 wt % EFdA + 50 wt % EVA | |
| --- | --- | --- | --- | --- | --- | --- | --- | --- | --- | --- |
| | avg (%) | std. dev. | avg (%) | std. dev. | avg (%) | std. dev. | avg (%) | std. dev. | avg (%) | std. dev. |
| 0.08 | 0.7 | 0.1 | 1.3 | 0.4 | 1.9 | 0.2 | 2.1 | 0.3 | 2.5 | 0.5 |
| 0.19 | 0.9 | 0.1 | 1.8 | 0.4 | 2.9 | 0.2 | 3.8 | 0.2 | 4.6 | 0.7 |
| 0.33 | 1.0 | 0.1 | 2.0 | 0.5 | 3.5 | 0.4 | 4.8 | 0.3 | 5.9 | 0.7 |
| 0.54 | 1.1 | 0.1 | 2.3 | 0.5 | 4.4 | 0.5 | 6.0 | 0.4 | 7.5 | 1.0 |
| 1 | 1.3 | 0.2 | 2.7 | 0.6 | 5.6 | 0.8 | 8.0 | 0.6 | 10.5 | 1.3 |
| 2 | 1.6 | 0.1 | 3.2 | 0.7 | 7.9 | 1.3 | 12.0 | 0.3 | 16.6 | 2.6 |
| 3 | 1.7 | 0.2 | 3.5 | 0.7 | 9.2 | 1.5 | 14.5 | 0.5 | 19.8 | 2.8 |
| 4 | 1.8 | 0.2 | 3.8 | 0.8 | 10.4 | 1.8 | 17.1 | 0.8 | 23.5 | 3.3 |
| 8 | 2.2 | 0.3 | 4.7 | 1.1 | 14.4 | 2.5 | 25.1 | 1.4 | 32.3 | 1.8 |
| 15 | 2.8 | 0.3 | 6.0 | 1.4 | 20.5 | 3.1 | 35.0 | 2.1 | 44.2 | 2.2 |
| 23 | 3.4 | 0.4 | 7.2 | 1.7 | 25.3 | 3.8 | 42.8 | 1.8 | 53.5 | 2.2 |
| 30 | 3.4 | 0.2 | 7.6 | 2.4 | 28.1 | 5.1 | 46.5 | 1.9 | 57.5 | 1.8 |
| 37 | 3.6 | 0.4 | 8.4 | 2.2 | 31.4 | 4.4 | 52.3 | 1.8 | 64.6 | 1.7 |
| 50 | 4.1 | 0.4 | 9.3 | 2.7 | 35.1 | 4.6 | 59.7 | 1.7 | 72.3 | 0.7 |
| 59 | 4.6 | 0.5 | 10.2 | 3.1 | 38.8 | 4.8 | 65.3 | 1.9 | 78.4 | 0.3 |
| 74 | 5.2 | 0.5 | 11.7 | 3.6 | 44.3 | 5.4 | 73.0 | 2.9 | 85.4 | 0.4 |
| 84 | 5.3 | 0.5 | 11.8 | 3.7 | 45.4 | 5.0 | 73.6 | 2.2 | 85.9 | 0.1 |
| 93 | 5.5 | 0.6 | 12.4 | 4.0 | 47.4 | 5.4 | 76.5 | 2.3 | 88.9 | 0.0 |
| 102 | 5.7 | 0.6 | 12.8 | 4.1 | 49.9 | 5.6 | 79.2 | 2.8 | 91.2 | 1.7 |
| 129 | 5.9 | 0.6 | 13.1 | 4.3 | 51.3 | 5.6 | 78.7 | 2.7 | | |
| 157 | 6.7 | 0.6 | 15.1 | 5.1 | 57.5 | 5.9 | 86.6 | 2.7 | | |

TABLE 3

4'-ethynyl-2-fluoro-2'-deoxyadenosine in vitro release rates from 30 wt %, 35 wt %, 40 wt %, 45 wt % and 50 wt % 4'-ethynyl-2-fluoro-2'-deoxyadenosine in EVA implants (normalized to a 40 mm long implant)

| Sample | Release Rate at day 30 (mg/day) | Release rate at day 60 (mg/day) | Release rate at day 90 (mg/day) | Release rate at 6 months (mg/day) |
| --- | --- | --- | --- | --- |
| 30 wt % EFdA + 70 wt % EVA | 0.03 | 0.02 | 0.02 | 0.01 |
| 35 wt % EFdA + 65 wt % EVA | 0.08 | 0.05 | 0.04 | 0.03 |
| 40 wt % EFdA + 60 wt % EVA | 0.30 | 0.21 | 0.17 | 0.12 |
| 45 wt % EFdA + 55 wt % EVA | 0.49 | 0.35 | 0.28 | 0.20 |
| 50 wt % EFdA + 50 wt % EVA | 0.67 | 0.48 | 0.39 | 0.27 |

EXAMPLE 2

Preparation and In Vitro Release of Implant Drug Delivery Systems Containing 50-80 Wt % 4'-Ethynyl-2-Fluoro-2'-Deoxyadenosine Implantable devices were prepared using an extrusion process. The first step involved mixing the dry, micronized powders of the active compound and the cryomilled EVA using a Turbula T2F mixer. Drug and polymer blends were prepared at 50, 60 and 80 wt % drug load. The 4'-ethynyl-2-fluoro-2'-deoxyadenosine and polymer blends were hot-melt extruded using a twin screw extruder through a 3 mm diameter die, and pulled to a diameter of approximately 1.9-2.3 mm. The screws contained predominately conveying elements with a single 90° mixing section. The 1st zone where the drug-polymer blends were introduced was water-cooled and maintained at room temperature. The temperature for zones 2-4 was 100° C. Extruded fibers with diameters between 1.9-2.3 mm were cut to a length of approximately 40 mm.

The in vitro release rate of 4'-ethynyl-2-fluoro-2'-deoxyadenosine was determined by incubating the implants segments, approximately 1 cm in length, in a glass vial containing phosphate buffered saline (PBS) at 37° C., and 50 rpm shaking in an Innova 42 incubator. The volume of PBS was sufficient to maintain sink conditions. Sink conditions are defined as the drug concentration maintained at or below ⅓ of the maximum solubility (drug concentration ≤0.45 mg/mL in PBS at 37° C.). Samples were removed (0.5 mL) at selected time points, and centrifuged at 20,800×g for 8 min. The supernatant was removed (0.4 mL), diluted 4-fold, and vortexed. Samples were assayed by HPLC (Agilent 1100 series). Analysis of a 6 µL volume was performed at 240 nm with a Supelco Ascentis® Express C18 column (100×4.6 mm, 2.7 µm). The mobile phase was 0.1% H$_3$PO$_4$ and 50:50 ACN:MeOH (83:17 v/v) at a flow rate of 1.5 mL/min (40° C.).

To determine degradation of 4'-ethynyl-2-fluoro-2'-deoxyadenosine by HPLC, a 6 µL volume was injected onto an Agilent Zorbax SB-Aq column (150×4.6 mm, 3.5 µm). The mobile phase was 0.1% H$_3$PO$_4$ and 50:50 ACN:MeOH with a flow rate of 1.0 mL/min (40° C.). The mobile phase gradient is shown in table 1.

All samples were calibrated to 0.5 mg/mL standard solutions of 4'-ethynyl-2-fluoro-2'-deoxyadenosine in 50:50 MeOH:H$_2$O.

TABLE 4

4'-ethynyl-2-fluoro-2'-deoxyadenosine in vitro release from 50%, 60%, and 80 wt % 4'-ethynyl-2-fluoro-2'-deoxyadenosine in EVA implants at sink conditions; reported as a % release from total [avg = average and std dev = standard deviation]

| Time (days) | 50 wt % EFdA + 50 wt % EVA | | 60 wt % EFdA + 40 wt % EVA | | 80 wt % EFdA + 20 wt % EVA | |
|---|---|---|---|---|---|---|
| | avg (%) | Std. Dev. | avg (%) | Std. Dev. | avg (%) | Std. Dev. |
| 3 | 10 | 3 | 18 | 4 | 38 | 3 |
| 7 | 19 | 2 | 34 | 4 | 62 | 3 |
| 14 | 27.1 | 0.6 | 49 | 2 | 93 | 2 |
| 21 | 35 | 1 | 61 | 3 | 112 | 1 |
| 27 | 37.6 | 0.5 | 65 | 2 | 106 | 1 |
| 35 | 42.6 | 0.4 | 73 | 2 | 106 | 1 |
| 42 | 45.8 | 0.3 | 79 | 2 | | |
| 49 | 48.9 | 0.2 | 83 | 2 | | |
| 63 | 58.9 | 0.3 | 97 | 2 | | |
| 101 | 79.4 | 0.6 | | | | |
| 122 | 83 | 2 | | | | |
| 136 | 89.6 | 0.6 | | | | |
| 149 | 94 | 1 | | | | |
| 163 | 93 | 2 | | | | |
| 175 | 97.5 | 0.2 | | | | |

TABLE 5

4'-ethynyl-2-fluoro-2'-deoxyadenosine in vitro release rates from 50% EFdA, 60% EFdA, and 80 wt % EFdA in 4'-ethynyl-2-fluoro-2'-deoxyadenosine in EVA implants (normalized to a 40 mm long implant) [n/d = not determined]

| Sample | Release rate at day 20 (mg/day) | Release rate at day 50 (mg/day) | Release rate at day 100 (mg/day) |
|---|---|---|---|
| 50 wt % EFdA + 50 wt % EVA | 0.61 | 0.39 | 0.27 |
| 60 wt % EFdA + 40 wt % EVA | 1.21 | 0.76 | n/d |
| 80 wt % EFdA + 20 wt % EVA | 3.19 | n/d | n/d |

EXAMPLE 3

Preparation and In Vivo Release of Implant Drug Delivery Systems Containing 40, 50, 60 and 80 Wt % 4'-Ethynyl-2-Fluoro-2'-Deoxyadenosine Implantable devices were prepared using an extrusion process. The first step involved mixing the dry, micronized powders of the active compound and the cryomilled EVA using a Turbula T2F mixer. Drug and polymer blends were prepared at 40, 50, 60 and 80 wt % drug load. The 4'-ethynyl-2-fluoro-2'-deoxyadenosine and polymer blends were hot-melt extruded using a twin screw extruder through a 3 mm diameter die, and pulled to a diameter of approximately 1.9-2.3 mm. The screws contained predominately conveying elements with a single 90° mixing section. The 1st zone where the drug-polymer blends were introduced was water-cooled and maintained at room temperature. The temperature for zones 2-4 was 100° C. Extruded fibers with diameters between 1.9-2.3 mm were cut to an appropriate length to achieve the desired amount of drug per implant for in vivo studies. All animal studies were conducted following protocols in accordance with the Institutional Animal Care and Use Committee (IACUC) at NIRC and Merck, which adhere to the regulations outlined in the USDA Animal Welfare Act. For each implantation, a Wistar Han rat was anesthetized using isoflurane to effect prior to subcutaneous dose administrations. Using a trocar needle, the solid formulation (~2 mm in diameter and of varying lengths based on the body weight of the individual animal to achieve the dose appropriate for each group) was placed in the scapular region. Four animals (2 males and 2 females) were used for each formulation. Animals were monitored until recovered. At indicated time points, samples of blood were obtained from anesthetized animals (using isoflurane) and processed to plasma for determination of 4'-ethynyl-2-fluoro-2'-deoxyadenosine levels.

TABLE 6

4'-ethynyl-2-fluoro-2'-deoxyadenosine concentration in blood plasma from 40%, 50%, 60%, and 80 wt % 4'-ethynyl-2-fluoro-2'-deoxyadenosine in EVA implants

| Time (days) | 40 wt % EFdA + 60 wt % EVA | | 50% EFdA + 50 wt % EVA | | 60% EFdA + 40 wt % EVA | | 80% EFdA + 20 wt % EVA | |
|---|---|---|---|---|---|---|---|---|
| | Avg. (nM) | Std. Dev. (nM) | Avg. (nM) | Std. Dev. (nM) | Avg. (nM) | Std. Dev. (nM) | Avg. (nM) | Std. Dev. (nM) |
| 0.04 | 319 | 107 | 1126 | 356 | 2205 | 174 | 3722 | 2995 |
| 0.08 | 190 | 92 | 642 | 297 | 1643 | 350 | 2503 | 2067 |
| 0.17 | 105 | 61 | 317 | 215 | 1286 | 768 | 2505 | 2579 |
| 0.29 | 70 | 21 | | | | | | |
| 1 | 38 | 16 | 225 | 115 | 589 | 81 | 1878 | 1445 |
| 2 | 25 | 11 | 220 | 37 | 505 | 68 | 1626 | 960 |
| 3 | 21 | 12 | 194 | 7 | 402 | 40 | 1184 | 424 |
| 4 | 17 | 9 | 179 | 20 | 379 | 52 | 1190 | 427 |
| 7 | 14 | 6 | 144 | 18 | 298 | 53 | 1162 | 410 |
| 10 | 13 | 5 | 111 | 19 | 213 | 27 | 698 | 202 |
| 14 | 9 | 3 | 91 | 15 | 197 | 13 | 428 | 105 |
| 17 | 9 | 2 | 84 | 10 | 186 | 13 | 381 | 93 |
| 21 | 5 | 3 | | | | | | |
| 22 | | | 63 | 16 | 148 | 12 | 270 | 140 |
| 25 | | | 57 | 15 | 129 | 11 | 227 | 142 |
| 28 | 3 | 1 | 55 | 11 | 112 | 10 | 170 | 129 |
| 31 | 4 | 2 | 48 | 9 | 109 | 8 | 159 | 139 |
| 35 | 3 | 3 | 57 | 11 | 119 | 16 | 187 | 21 |

TABLE 6-continued

4'-ethynyl-2-fluoro-2'-deoxyadenosine concentration in blood plasma from 40%, 50%, 60%, and 80 wt % 4'-ethynyl-2-fluoro-2'-deoxyadenosine in EVA implants

| Time (days) | 40 wt % EFdA + 60 wt % EVA | | 50% EFdA + 50 wt % EVA | | 60% EFdA + 40 wt % EVA | | 80% EFdA + 20 wt % EVA | |
|---|---|---|---|---|---|---|---|---|
| | Avg. (nM) | Std. Dev. (nM) | Avg. (nM) | Std. Dev. (nM) | Avg. (nM) | Std. Dev. (nM) | Avg. (nM) | Std. Dev. (nM) |
| 38 | | | 51 | 13 | 91 | 7 | 129 | 18 |
| 42 | | | 47 | 13 | 99 | 10 | 117 | 5 |
| 44 | 4 | 2 | | | | | | |
| 45 | | | 45 | 16 | 85 | 11 | 66 | 55 |
| 51 | 3 | 2 | | | | | | |
| 53 | | | 51 | 14 | 78 | 23 | | |
| 60 | | | 36 | 13 | 64 | 4 | | |
| 64 | | | 38 | 10 | 59 | 10 | | |
| 65 | 3 | 1 | | | | | | |
| 72 | 3 | 1 | | | | | | |
| 74 | | | 37 | 10 | 55 | 12 | | |
| 78 | | | 32 | 9 | 34 | 5 | | |
| 79 | 3 | 1 | | | | | | |
| 85 | | | 31 | 7 | 12 | 8 | | |
| 86 | 3 | 1 | | | | | | |
| 92 | | | 28 | 7 | 6 | n/a | | |
| 98 | 3 | 2 | | | | | | |
| 106 | | | 32 | 8 | | | | |
| 113 | | | 27 | 7 | | | | |
| 120 | | | 25 | 3 | | | | |
| 127 | | | 25 | 2 | | | | |
| 134 | | | 25 | 5 | | | | |
| 141 | | | 21 | 5 | | | | |
| 148 | | | 23 | 3 | | | | |
| 155 | | | 19 | 6 | | | | |
| 162 | | | 22 | 7 | | | | |
| 169 | | | 18 | 4 | | | | |
| 176 | | | 21 | 2 | | | | |
| 183 | | | 18 | 5 | | | | |
| 190 | | | 18 | 3 | | | | |
| 197 | | | 17 | 3 | | | | |
| 204 | | | 17 | 1 | | | | |
| 211 | | | 15 | 2 | | | | |
| 218 | | | 13 | 6 | | | | |
| 225 | | | 12 | 8 | | | | |
| 232 | | | 15 | 3 | | | | |
| 239 | | | 13 | 0 | | | | |
| 246 | | | 11 | 1 | | | | |
| 253 | | | 11 | 0 | | | | |
| 260 | | | 10 | 2 | | | | |
| 269 | | | 8 | 5 | | | | |

TABLE 7

4'-ethynyl-2-fluoro-2'-deoxyadenosine in vivo release rates from 40%, 50%, 60%, and 80 wt % 4'-ethynyl-2-fluoro-2'-deoxyadenosine in EVA implants (normalized to a 40 mm long implant) [n/d = not determined]

| Sample | Release rate at day 25 (mg/day) | Release rate at day 50 (mg/day) | Release rate at day 100 (mg/day) |
|---|---|---|---|
| 40 wt % EFdA + 60 wt % EVA | 0.014 | 0.012 | 0.009 |
| 50 wt % EFdA + 50 wt % EVA | 0.18 | 0.15 | 0.094 |
| 60 wt % EFdA + 40 wt % EVA | 0.39 | 0.25 | 0.036 |
| 80 wt % EFdA + 20 wt % EVA | 0.69 | n/d | n/d |

EXAMPLE 4

Preparation and In Vitro Release of Implant Drug Delivery Systems Containing 4'-Ethynyl-2-Fluoro-2'-Deoxyadenosine with a Radiopaque Agent Implants were prepared using an extrusion process. The micronized polymer, 4'-ethynyl-2-fluoro-2'-deoxyadenosine, and $BaSO_4$ were blended at various ratios: 40 and 45 wt % drug in EVA, and 35 and 40 wt % drug with 10 wt % $BaSO_4$ in EVA. The preblend was melt extruded with a twin screw extruder at temperatures ranging from 100-140° C., screw speed at 30 rpm, and then pelletized. The pellets were then extruded with a single screw extruder with temperatures ranging from 110-140° C., and screw speed at 20-25 rpm to form a 2±0.05 mm diameter filament, and then cut to a length of 40±2 mm.

The in vitro release rate of 4'-ethynyl-2-fluoro-2'-deoxyadenosine was determined by incubating the implants segments, approximately 1 cm in length, in a glass vial containing phosphate buffered saline (PBS) at 37° C., and 50 rpm shaking in an Innova 42 incubator. The volume of PBS was sufficient to maintain sink conditions. Sink conditions are defined as the drug concentration maintained at or below ⅓ of the maximum solubility (drug concentration ≤0.45 mg/mL in PBS at 37° C.). Samples were removed (0.5 mL) at selected time points, and centrifuged at 20,800×g for 8 min. The supernatant was removed (0.4 mL), diluted 4-fold, and vortexed. Samples were assayed by HPLC (Agilent 1100 series). Analysis of a 6 µL volume was performed at 240 nm with a Supelco Ascentis® Express C18 column (100×4.6 mm, 2.7 µm). The mobile phase was 0.1% $H_3PO_4$ and 50:50 ACN:MeOH (83:17 v/v) at a flow rate of 1.5 mL/min (40° C.).

To determine degradation of 4'-ethynyl-2-fluoro-2'-deoxyadenosine by HPLC, a 6 µL volume was injected onto an Agilent Zorbax SB-Aq column (150×4.6 mm, 3.5 µm). The mobile phase was 0.1% $H_3PO_4$ and 50:50 ACN:MeOH with a flow rate of 1.0 mL/min (40° C.). The mobile phase gradient is shown in table 1.

All samples were calibrated to 0.5 mg/mL standard solutions of 4'-ethynyl-2-fluoro-2'-deoxyadenosine in 50:50 MeOH:$H_2O$.

EXAMPLE 5

Preparation and In Vivo Release of Implant Drug Delivery Systems Containing 4'-Ethynyl-2-Fluoro-2'-Deoxyadenosine with a Radiopaque Agent Implants were prepared using an extrusion process. The micronized polymer, 4'-ethynyl-2-fluoro-2'-deoxyadenosine, and $BaSO_4$ were blended at various ratios: 40 and 45 wt % drug in EVA, and 35 and 40 wt % drug with 10 wt % $BaSO_4$ in EVA. The preblend was melt extruded with a twin screw extruder at temperatures ranging from 100-140° C., screw speed at 30 rpm, and then pelletized. The pellets were then extruded with a single screw extruder with temperatures ranging from 110-140° C., and screw speed at 20-25 rpm to form a 2±0.05 mm diameter filament, and then cut to the appropriate length to achieve the desired amount of drug per implant for in vivo studies. All animal studies were conducted following protocols in accordance with the Institutional Animal Care and Use Committee (IACUC) at NIRC and Merck, which adhere to the regulations outlined in the USDA Animal Welfare Act. For each implantation, a Wistar Han rat was anesthetized using isoflurane to effect prior to subcutaneous dose administrations. Using a trocar needle, the solid formulation (~2 mm in diameter and of varying lengths based on the body weight of the individual animal to achieve the dose appropriate for each group) was placed in the scapular region. Four animals (2 males and 2 females) were used for each formulation. Animals were monitored until recovered. At indicated time points, samples of blood were obtained from anesthetized animals (using isoflurane) and processed to plasma for determination of 4'-ethynyl-2-fluoro-2'-deoxyadenosine levels.

TABLE 8

4'-ethynyl-2-fluoro-2'-deoxyadenosine in vitro release from 35 wt % EFdA (with 10 wt % $BaSO_4$), 40 wt % EFdA (with and without 10 wt % $BaSO_4$), and 45 wt % EFdA in EVA implants at sink conditions

| Time (days) | 35 wt % EFdA + 10 wt % $BaSO_4$ + 55 wt % EVA | | 40 wt % EFdA + 60 wt % EVA | | 40 wt % EFdA + 10 wt % $BaSO_4$ + 50 wt % EVA | | 45 wt % EFdA + 55 wt % EVA | |
|---|---|---|---|---|---|---|---|---|
| | Avg (%) | std. dev. | Avg (%) | std. dev. | Avg (%) | std. dev. | Avg (%) | std. dev. |
| 0.08 | 1.70 | 0.09 | 1.71 | 0.03 | 2.20 | 0.09 | 2.06 | 0.04 |
| 0.17 | 1.92 | 0.02 | 2.04 | 0.05 | 2.75 | 0.06 | 2.64 | 0.06 |
| 0.33 | 2.14 | 0.03 | 2.29 | 0.06 | 3.16 | 0.06 | 3.09 | 0.09 |
| 1.25 | 3.57 | 0.06 | 3.71 | 0.09 | 5.62 | 0.12 | 5.56 | 0.22 |
| 2.25 | 4.14 | 0.07 | 4.46 | 0.08 | 7.37 | 0.18 | 7.17 | 0.23 |
| 4 | 4.91 | 0.11 | 5.26 | 0.06 | 9.16 | 0.15 | 9.03 | 0.38 |
| 11 | 7.37 | 0.18 | 7.78 | 0.08 | 14.37 | 0.21 | 14.23 | 0.38 |
| 21 | 9.51 | 0.19 | 10.14 | 0.10 | 19.05 | 0.26 | 18.99 | 0.41 |
| 39 | 12.06 | 0.26 | 13.09 | 0.17 | 25.15 | 0.76 | 24.86 | 0.45 |
| 66 | 14.62 | 0.23 | 16.12 | 0.16 | 30.40 | 0.25 | 30.96 | 0.23 |
| 80 | 14.43 | 0.22 | 15.95 | 0.15 | 29.68 | 0.23 | 30.45 | 0.27 |
| 94 | 16.31 | 0.24 | 18.12 | 0.15 | 33.62 | 0.21 | 34.58 | 0.30 |

TABLE 9

4'-ethynyl-2-fluoro-2'-deoxyadenosine in vitro release rates from 35 wt % EFdA (with 10 wt % $BaSO_4$), 40 wt % EFdA (with and without 10 wt % $BaSO_4$), and 45 wt % EFdA in EVA implants (normalized to a 40 mm long implant)

| Sample | Release rate at day 30 (mg/day) | Release rate at day 60 (mg/day) | Release rate at day 90 (mg/day) | Release rate at 6 months (mg/day) |
|---|---|---|---|---|
| 35 wt % EFdA + 10 wt % $BaSO_4$ + 55 wt % EVA | 0.08 | 0.06 | 0.05 | 0.03 |
| 40 wt % EFdA + 60 wt % EVA | 0.10 | 0.07 | 0.06 | 0.04 |
| 40 wt % EFdA + 10 wt % $BaSO_4$ + 50 wt % EVA | 0.20 | 0.14 | 0.12 | 0.08 |
| 45 wt % EFdA + 55 wt % EVA | 0.21 | 0.15 | 0.12 | 0.09 |

FIG. 1 shows an x-ray image of an implant containing barium sulfate in a rat after a 6 month duration.

TABLE 10

4'-ethynyl-2-fluoro-2'-deoxyadenosine concentration in blood plasma from 35 wt % EFdA (with 10 wt % BaSO₄), 40 wt % EFdA (with and without 10 wt % BaSO₄), and 45 wt % EFdA in EVA implants

| Time (days) | 35 wt % EFdA + 10 wt % BaSO₄ + 55 wt % EVA | | 40 wt % EFdA + 60 wt % EVA | | 40 wt % EFdA + 10 wt % BaSO₄ + 50 wt % EVA | | 45 wt % EFdA + 55 wt % EVA | |
|---|---|---|---|---|---|---|---|---|
|  | avg (nM) | std. dev. (nM) | avg (nM) | std. dev. (nM) | avg (nM) | std. dev. (nM) | avg (nM) | std. dev. (nM) |
| 0.041666667 | 1128 | 396 | 1418 | 500 | 2395 | 583 | 2090 | 303 |
| 0.083333333 | 592 | 218 | 715 | 243 | 1306 | 394 | 1163 | 228 |
| 0.166666667 | 228 | 75 | 271 | 72 | 505 | 129 | 502 | 99 |
| 1 | 51 | 14 | 55 | 12 | 110 | 13 | 122 | 22 |
| 2 | 32 | 10 | 36 | 7 | 71 | 12 | 95 | 22 |
| 9 | 13 | 3 | 15 | 4 | 34 | 5 | 45 | 4 |
| 11 | 10 | 2 | 15 | 4 | 32 | 6 | 43 | 7 |
| 16 | 9 | 2 | 10 | 2 | 25 | 5 | 32 | 4 |
| 18 | 9 | 1 | 9 | 3 | 23 | 4 | 31 | 6 |
| 23 | 6 | 2 | 8 | 3 | 19 | 4 | 24 | 4 |
| 25 | 6 | 2 | 7 | 2 | 18 | 4 | 22 | 3 |
| 30 | 5 | 2 | 6 | 1 | 14 | 3 | 20 | 3 |
| 32 | 5 | 1 | 6 | 1 | 14 | 6 | 18 | 2 |
| 37 | 4 | 1 | 6 | 1 | 12 | 3 | 15 | 4 |
| 39 | 5 | 1 | 5 | 1 | 12 | 3 | 15 | 3 |
| 44 | 4 | 1 | 5 | 1 | 10 | 3 | 12 | 2 |
| 46 | 4 | 1 | 5 | 1 | 10 | 2 | 13 | 3 |
| 51 | 4 | 1 | 5 | 2 | 10 | 3 | 12 | 2 |
| 58 | 3 | 1 | 4 | 2 | 9 | 1 | 11 | 2 |
| 65 | 4 | 2 | 4 | 0 | 8 | 2 | 11 | 2 |
| 72 | 3 | 1 | 4 | 1 | 9 | 3 | 11 | 3 |
| 79 | 4 | 2 | 4 | 1 | 7 | 2 | 9 | 3 |
| 87 | 4 | 1 | 3 | 1 | 7 | 3 | 10 | 4 |
| 93 | 4 | 2 | 3 | 1 | 7 | 2 | 10 | 4 |
| 100 | 3 | 2 | 3 | 1 | 6 | 2 | 9 | 3 |
| 107 | 3 | 1 | 3 | 1 | 6 | 1 | 9 | 2 |
| 114 | 4 | 1 | 3 | 1 | 6 | 1 | 9 | 2 |
| 121 | 2 | 1 | 3 | 1 | 5 | 2 | 7 | 2 |
| 128 | 2 | 1 | 2 | 1 | 4 | 1 | 7 | 2 |
| 135 | 2 | 1 | 2 | 1 | 5 | 2 | 7 | 2 |
| 142 | 2 | 1 | 2 | 0 | 5 | 1 | 8 | 3 |
| 149 | 2 | 1 | 3 | 1 | 5 | 1 | 6 | 2 |
| 156 | 2 | 1 | 2 | 1 | 4 | 2 | 6 | 1 |
| 163 | 2 | 1 | 2 | 1 | 5 | 2 | 6 | 1 |
| 170 | 2 | 1 | 3 | 1 | 4 | 1 | 7 | 2 |
| 177 | 2 | 1 | 3 | 1 | 4 | 1 | 5 | 1 |
| 182 | 2 | 1 | 2 | 1 | 3 | 1 | 6 | 1 |

TABLE 11

4'-ethynyl-2-fluoro-2'-deoxyadenosine in vivo release rates from 35 wt % EFdA (with 10 wt % BaSO₄), 40 wt % EFdA (with and without 10 wt % BaSO₄), and 45 wt % EFdA in EVA implants (normalized to a 40 mm long implant)

| Sample | Release rate at day 30 (mg/day) | Release rate at day 60 (mg/day) | Release rate at day 127 (mg/day) | Release rate at 6 months (mg/day) |
|---|---|---|---|---|
| 35 wt % EFdA + 10 wt % BaSO₄ + 55 wt % EVA | 0.025 | 0.016 | 0.009 | 0.010 |
| 40 wt % EFdA + 60 wt % EVA | 0.027 | 0.020 | 0.011 | 0.010 |
| 40 wt % EFdA + 10 wt % BaSO₄ + 50 wt % EVA | 0.064 | 0.039 | 0.022 | 0.016 |
| 45 wt % EFdA + 55 wt % EVA | 0.095 | 0.050 | 0.031 | 0.026 |

EXAMPLE 6

Preparation and In Vivo Studies of Implant Drug Delivery Systems Containing 45 Wt % 4'-Ethynyl-2-Fluoro-2'-Deoxyadenosine Implants were prepared using an extrusion process. The micronized polymer, and 4'-ethynyl-2-fluoro-2'-deoxyadenosine were blended at 45 wt % drug in EVA. The preblend was melt extruded with a twin screw extruder at temperatures ranging from 100–140° C., screw speed at 30 rpm, and then pelletized. The pellets were then extruded with a single screw extruder with temperatures ranging from 110-140° C., and screw speed at 20-25 rpm to form a 2±0.05 mm diameter filament, and then cut to a length of 40±2 mm.

All animal studies were conducted following protocols in accordance with the Institutional Animal Care and Use Committee (IACUC) at NIRC and Merck, which adhere to the regulations outlined in the USDA Animal Welfare Act. For each implantation, a Rhesus monkey was sedated with Ketamine HCl (100 mg/mL) prior to subcutaneous implant administrations. Using an injector device, the implant was placed subcutaneously in the interscapular region. Eight animals (4 males and 4 females) were used. Animals were monitored until recovered. At indicated time points, samples of blood were obtained and processed to plasma for determination of 4'-ethynyl-2-fluoro-2'-deoxyadenosine levels.

TABLE 12

4'-ethynyl-2-fluoro-2'-deoxyadenosine concentration in blood plasma from 45 wt % 4'-ethynyl-2-fluoro-2'-deoxyadenosine in EVA implants

| | 45 wt % EFdA + 55 wt % EVA | |
|---|---|---|
| Time (days) | Avg (nM) | std. dev. (nM) |
| 0.020833 | 237 | 50 |
| 0.041667 | 256 | 41 |
| 0.083333 | 203 | 25 |
| 0.166667 | 118 | 19 |
| 0.25 | 86 | 14 |
| 1 | 40 | 6 |
| 2 | 31 | 5 |
| 3 | 26 | 5 |
| 7 | 17 | 3 |
| 14 | 12 | 2 |
| 23 | 9 | 2 |
| 37 | 6 | 1 |
| 51 | 5 | 1 |
| 65 | 5 | 1 |
| 79 | 4 | 1 |
| 107 | 4 | 1 |
| 127 | 2.7 | 0.4 |

TABLE 13

4'-ethynyl-2-fluoro-2'-deoxyadenosine in vivo release rates from 45 wt % 4'-ethynyl-2-fluoro-2'-deoxyadenosine in EVA implants

| Sample | Release rate at day 30 (mg/day) | Release rate at day 60 (mg/day) | Release rate at day 90 (mg/day) | Release rate at 120 days (mg/day) |
|---|---|---|---|---|
| 45 wt % EFdA + 55 wt % EVA | 0.18 | 0.12 | 0.10 | 0.076 |

EXAMPLE 7

Preparation and In Vivo Studies of Implant Drug Delivery Systems Containing 50 wt % 4'-Ethynyl-2-Fluoro-2'-Deoxyadenosine Implants were prepared by extrusion of a 45:55 4'-ethynyl-2-fluoro-2'-deoxyadenosine: EVA at elevated temperature yielding fibers having diameters between 2.00±0.05 mm that were cut to 40±2 mm for in vivo studies. All animal studies were conducted following protocols in accordance with the Institutional Animal Care and Use Committee (IACUC) at NIRC and Merck, which adhere to the regulations outlined in the USDA Animal Welfare Act. For each implantation, a Rhesus monkey was sedated with Ketamine HCl (100 mg/mL) prior to subcutaneous dose administrations. Using an injector device, the implant was placed subcutaneously in the interscapular region. Three animals (all males) were used. Animals were monitored until recovered. At indicated time points, samples of blood were obtained and processed to plasma for determination of 4'-ethynyl-2-fluoro-2'-deoxyadenosine levels.

TABLE 14

4'-ethynyl-2-fluoro-2'-deoxyadenosine concentration in blood plasma from 50 wt % 4'-ethynyl-2-fluoro-2'-deoxyadenosine in EVA implants

| | 50 wt % EFdA + 50 wt % EVA | |
|---|---|---|
| Time (days) | Avg (nM) | std. dev. (nM) |
| 0.08 | 117 | 39 |
| 0.17 | 86 | 33 |
| 0.25 | 74 | 23 |
| 1 | 49 | 3 |
| 2 | 33 | 3 |
| 9 | 19 | 4 |
| 16 | 13 | 2 |
| 30 | 10 | 2 |
| 44 | 8 | 2 |
| 58 | 8 | 1 |
| 72 | 8 | 0 |
| 86 | 7 | 1 |
| 100 | 6 | 1 |
| 114 | 5.2 | 0.8 |

TABLE 15

4'-ethynyl-2-fluoro-2'-deoxyadenosine in vivo release rates from 50 wt % 4'-ethynyl-2-fluoro-2'-deoxyadenosine in EVA implants

| Sample | Release rate at day 30 (mg/day) | Release rate at day 60 (mg/day) | Release rate at day 114 (mg/day) |
|---|---|---|---|
| 50 wt % EFdA + 50 wt % EVA | 0.57 | 0.43 | 0.29 |

What is claimed is:

1. A monolithic implant drug delivery system comprising between 30% and 50% by weight of 4'-ethynyl-2-fluoro-2'-deoxyadenosine, a radiopaque material and ethylene vinyl acetate copolymer, wherein the 4'-ethynyl-2-fluoro-2'-deoxyadenosine is dispersed or dissolved in the ethylene vinyl acetate copolymer, and wherein said implant drug delivery system is implanted subdermally and 4'-ethynyl-2-fluoro-2'-deoxyadenosine is continually released in vivo at a rate resulting in a plasma concentration between 0.02 ng/mL and 300.0 ng/mL.

2. The implant drug delivery system of claim 1 wherein the 4'-ethynyl-2-fluoro-2'-deoxyadenosine plasma concentration is between 0.02 ng/mL and 30.0 ng/mL.

3. The implant drug delivery system of claim 2 wherein the 4'-ethynyl-2-fluoro-2'-deoxyadenosine the plasma concentration is between 0.02 ng/mL and 8.0 ng/mL.

4. The implant drug delivery system of claim 1 wherein the ethylene vinyl acetate copolymer is selected from the group consisting ethylene vinyl acetate copolymer (9% vinyl acetate), ethylene vinyl acetate copolymer (15% vinyl acetate), ethylene vinyl acetate copolymer (28% vinyl acetate), and ethylene vinyl acetate copolymer (33% vinyl acetate).

5. The implant drug delivery system of claim 4 wherein the ethylene vinyl acetate copolymer is ethylene vinyl acetate copolymer (9% vinyl acetate).

6. The implant drug delivery system of claim 4 wherein the ethylene vinyl acetate copolymer is ethylene vinyl acetate copolymer (15% vinyl acetate).

7. The implant drug delivery system of claim 1 comprising between 1% and 20% by weight of a radiopaque material.

8. The implant drug delivery system of claim 1 wherein the 4'-ethynyl-2-fluoro-2'-deoxyadenosine is released at therapeutic concentrations for a duration from between three months and thirty-six months.

9. The implant drug delivery system of claim 1 wherein the 4'-ethynyl-2-fluoro-2'-deoxyadenosine is released at prophylactic concentrations for a duration from between three months and thirty-six months.

\* \* \* \* \*